United States Patent [19]
Nevo

[11] Patent Number: 5,634,467
[45] Date of Patent: Jun. 3, 1997

[54] METHOD AND APPARATUS FOR ASSESSING CARDIOVASCULAR PERFORMANCE

[75] Inventor: Erez Nevo, Kiryat Bialik, Israel

[73] Assignee: Robin Medical Technologies, Nesher, Israel

[21] Appl. No.: 332,946

[22] Filed: Nov. 1, 1994

[30] Foreign Application Priority Data

Nov. 8, 1993 [IL] Israel ......................................... 107540

[51] Int. Cl.$^6$ ................................................. A61B 5/029
[52] U.S. Cl. .......................... 128/672; 128/670; 128/677; 128/683
[58] Field of Search ...................................... 128/670, 672, 128/677, 680, 681, 683, 687, 688

[56] References Cited

U.S. PATENT DOCUMENTS

| | | | |
|---|---|---|---|
| 4,137,910 | 2/1979 | Murphy | 128/205 |
| 4,877,035 | 10/1989 | Bogen et al. | 128/673 |
| 5,199,438 | 4/1993 | Pearlman | 128/670 |
| 5,241,965 | 9/1993 | Mick | 128/691 |
| 5,445,159 | 8/1995 | Cheng | 128/672 |

FOREIGN PATENT DOCUMENTS

| | | |
|---|---|---|
| 420 085 | 4/1991 | European Pat. Off. . |
| 89/07414 | 8/1989 | WIPO . |
| 91/13589 | 9/1991 | WIPO . |

*Primary Examiner*—Angela D. Sykes
*Assistant Examiner*—Stephen Huang
*Attorney, Agent, or Firm*—Benjamin Barish

[57] ABSTRACT

A method of assessing the cardiovascular performance of a subject, by: applying periodically, in synchronism with every $n^{th}$ heart cardiac cycle wherein "n" is at least two, external pressure pulsations on a peripheral organ of the subject sufficient to alter ventricular loading; acquiring data representative of the ventricular pressure, and data representative of the ventricular volume, of the subject's heart over a plurality of heart cardiac cycles; and utilizing such data for assessing the cardiovascular performance of the subject. Ventricular loading may be altered by impeding ventricular ejection (changing afterload), and/or by altering venous return to the heart (changing preload).

18 Claims, 7 Drawing Sheets

ELECTRO-
CARDIOGRAM

TIME

FIG. 3B

EXTERNAL
PRESSURE
PULSATIONS

TIME

FIG. 3C

AORTIC
BLOOD
FLOW

TIME

FIG. 3D

ARTERIAL
BLOOD
PRESSURE

TIME

VENTRICULAR (AORTIC) PRESSURE

FIG. 7A2

VENTRICULAR VOLUME

FIG. 7B $$E_{max} = \text{Slope of ESPVR} = \frac{P_{es2} - P_{es1}}{ESV_2 - ESV_1}$$

VENTRICULAR (AORTIC) PRESSURE

VENTRICULAR VOLUME

FIG. 8A

ELECTRO-CARDIOGRAM

TIME

FIG. 8B

EXTERNAL PRESSURE PULSATIONS

TIME

FIG. 8C

AORTIC BLOOD FLOW

TIME

FIG. 8D

ARTERIAL BLOOD PRESSURE

TIME

FIG. 9

VENTRICULAR (AORTIC) PRESSURE

VENTRICULAR VOLUME

METHOD AND APPARATUS FOR ASSESSING CARDIOVASCULAR PERFORMANCE

FIELD AND BACKGROUND OF THE INVENTION

The present invention relates to a method and apparatus for assessing the cardiovascular performance of a subject, particularly for diagnosing and/or monitoring treatment of patients with ischemic heart diseases (IHD) or with heart failure (HF).

Ischemic heart disease (IHD) is one of the major causes of morbidity and mortality in the developed countries. About 900,000 new patients of IHD are diagnosed every year in the USA. Many of these patients consequently suffer from reduced performance of the cardiovascular system (CVS) which deteriorates towards the clinical stage of heart failure (HF). Currently, about two milion patients have congestive HF in the USA; this number is expected to increase substantially. Patients with severe HF are limited in their daily life, are not capable of performing simple activities, and are hospitalized very often because of acute exacerbations of their disease. In addition to the sociologic impact of the disease, it has an enormous economical cost, including costs for expensive drug therapy, high rate of hospitalization costs, and loss of working days by the hospitalized or the medically-limited patients. About 35% of all patients with HF are hospitalized every year.

Large scale, multi-center therapy trials demonstrated that the mechanical performance of the heart is a major determinant of prognosis in HF patients and in patients with left-ventricular dysfunction after myocardial infarct. Other studies showed that the mechanical performance is an important determinant of functional capacity of these patients, although the interrelation between the two is more complex.

In addition to its role in prognosis assessment, the classification of HF severity is of importance in planning therapy. Drug therapy for HF patients is initiated with the following major goals: to relieve symptoms, to improve the quality of life, and to prolong life. Consequently, drugs are tested for their direct effect on functional capacity, e.g., by showing an improvement of exercise stress test performance, and by showing longer survival when compared with traditional therapy. However, large variations between individual subjects may modify their response to the standard drug therapy and result in a non-optimal effect. Thus the individual response to the therapy has to be monitored by follow-up evaluations, and appropriate adjustments in therapy may be required.

Unfortunately, current indices for non-invasive assessment of CVS mechanical performance, e.g., Ejection Fraction (EF), are inherently limited and may provide only weak correlations with functional capacity and quality of life. Nevertheless, the simplicity of non-invasive EF measurement makes it the most common index for the assessment of CVS performance.

A more accurate characterization can be based on a well established description of the CVS, which evolved from many years of physiological and pathophysiological research. The traditional framework is based on four main determinants of global CVS performance: myocardial contactility, ventricular preload, vascular load, and heart rate. For routine application in the clinical practice, these determinants have to be quantified by simple, non-invasive indices. An ideal index should be highly sensitive to the specific determinant and not sensitive to the other determinants. While indices for preload, afterload and heart rate are relatively easy to determine, a good index of myocardial contractility has been found to be more problemmatical.

The ventricular elastance, or end-systolic elastance (Ees), has been suggested as an index of myocardial contractility which is relatively independent on the other determinants. This index is physiologically related to the classical Frank-Starling Law, which constitutes the basis for the quantitative analysis of CVS performance. Since then, the index Ees was evaluated in numerous studies and became a well accepted index of myocardial contactility.

U.S. Pat. No. 4,877,035, which is hereby incorporated by reference, discloses a technique for determining the end-systolic elastance (Ees) of a subject's heart by measuring the end-systolic pressure-volume relation in which the afterload is varied by the controlled inflation of an intraaortic balloon catheter positioned in the ascending aorta. Balloon inflation is timed to transiently interrupt ventricular ejection at different times during the ejection phase, producing contraction at different ventricular volumes. Simultaneous measurements of left ventricular pressure and aortic volume during the occlusion sequence allows pressure vs. ejected volume loops to be generated, from which the slope of the end-systolic pressure-volume relationship can be determined.

The technique described in the above patent, however, is extremely limited in clinical practice because of the complex invasive procedure required, namely the introduction and controlled inflation of the intraaortic balloon.

OBJECTS AND BRIEF SUMMARY OF THE INVENTION

An object of the present invention is to provide a novel, non-invasive method, and also an apparatus, for assessing the cardiovascular performance of a subject.

According to the present invention, there is provided a method of assessing the cardiovascular performance of a subject, comprising: applying periodically, in synchronism with every $n^{th}$ heart cardiac cycle wherein "n" is at least two, external pressure pulsations by a pressure applicator applied externally of the subject's body, on a peripheral organ of the subject sufficient to alter ventricular loading; acquiring data representative of the ventricular pressure, and data representative of the ventricular volume, of the subject's heart over a plurality of heart cardiac cycles; and utilizing the data for assessing the cardiovascular performance of the subject.

The ventricular loading may be altered by impeding ventricular ejection (changing afterload), and/or by altering venous return (changing preload).

The invention also provides apparatus for assessing the cardiovascular performance of a subject in accordance with the above method.

As will be described more particularly below, the method and apparatus can be implemented in a fully non-invasive manner thereby greatly extending its potential use in routine clinical practice.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
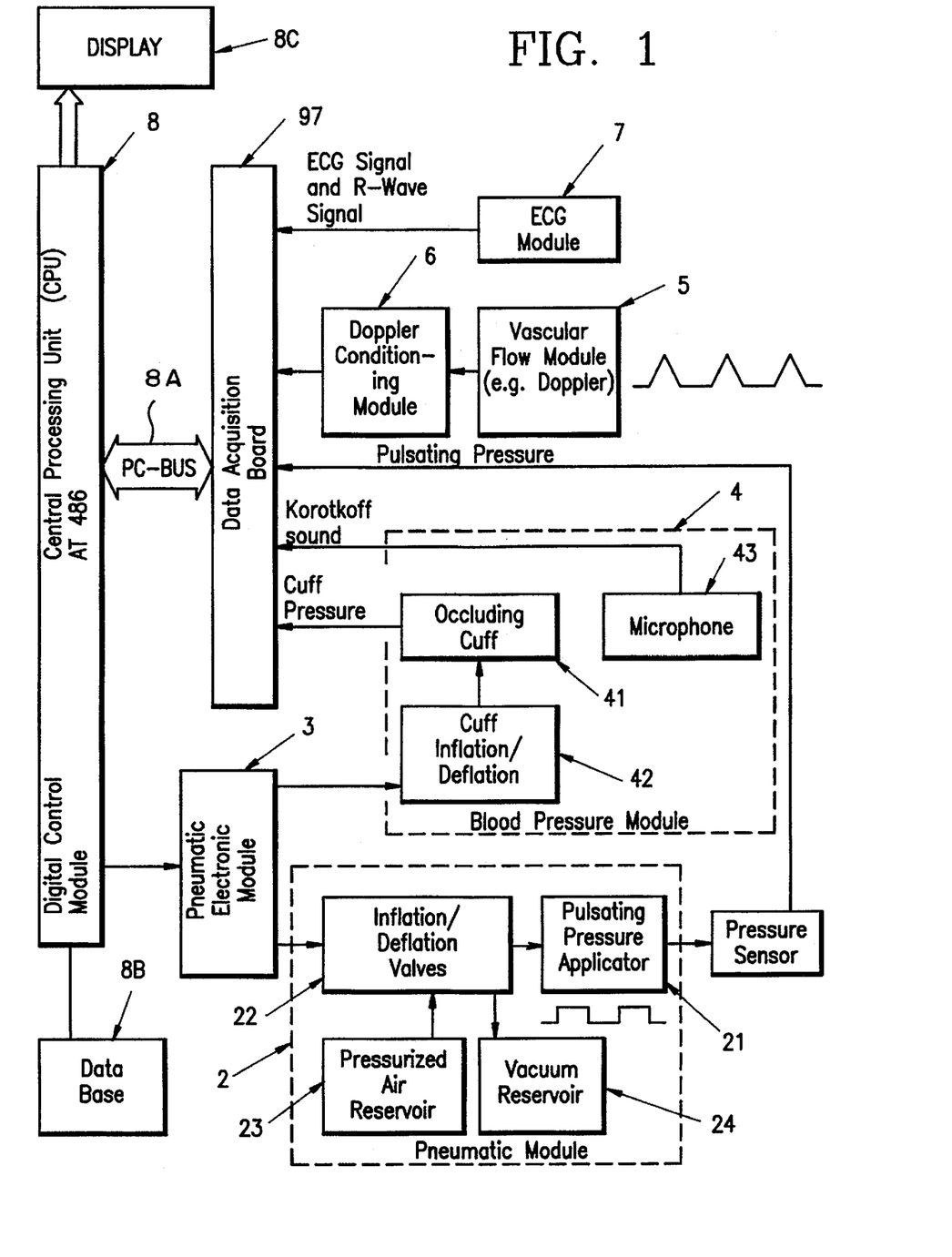
FIG. 1 is a block diagram illustrating the main components of one form of apparatus constructed in accordance with the present invention.

The apparatus illustrated in FIG. 1 comprises a pneumatic module, generally designated 2, which applies external pressure pulsations to a peripheral organ of a subject, such as a limb (e.g., arm or leg) or the lower abdomen, sufficient to alter ventricular loading. The pneumatic module 2 is controlled by an electronic control module 3, as will be described more particularly below.

The illustrated apparatus also includes a blood pressure module 4 which measures the blood pressure of the subject; a vascular flow module 5, and a Doppler conditioning module 6, for measuring the aortic flow rate of the subject; and an ECG module 7 which detects the ECG signal of the subject's heart. The external pressure pulsations applied by the pneumatic module 2 are synchronized with the heart cardiac cycle, as will be described more particularly below.

All the foregoing modules are controlled by a data processor including a central processing unit (CPU) 8, which communicates directly with the pneumatic control module 3, and with the other modules via a data acquisition board 9 and a PC bus 8a. The CPU 8 is supplied with data from a database 8b, and controls a display 8c.

The pneumatic module 2 applies pulsating external pressures on the lower body (e.g., lower limb and/or abdomen) via a pulsating pressure applicator unit 21. The latter unit includes a plurality of pressurized chambers incorporated in a pressure suit or pressure cuff(s) to be applied externally at the subject's body. The pulsating pressure applicator unit 21 communicates, via an inflation/deflation valve unit 22, with a pressurized air reservoir 23 and with a vacuum reservoir 24. Valve unit 22 includes a valve for each chamber connecting the respective chamber either to the pressurized air reservoir 23 for inflating the chamber, or to the vacuum reservoir 24 for deflating the chamber. The valves within unit 22 are preferably solenoid valves controlled by the CPU via the pneumatic control module 3.

Pneumatic control module 3 includes pressure sensors with signal conditioning circuitry (amplification and filtration), and solenoid relays. The pressure sensors (e.g., MPX2050, Motorola, USA) measure the pressure in the pneumatic chambers of the pulsating pressure chamber unit 21. The sensor outputs are amplified and low-pass filtered (3 dB at 40 Hz), and then interfaced to the CPU 8. The solenoid relays within module 3 control the inflation/deflation valves 22 to achieve the required time-pattern of pressure in the pressure chambers of the pressure applicator unit 21.

The blood pressure module 4 measures the arterial blood pressure non-invasively by the sphygmomanometry (Riva-Rocci) method, or by an equivalent method. The blood flow in the peripheral organ of the subject, e.g., a limb, is transiently occluded by the inflation of an occluding cuff 41 surrounding the limb (or other organ). The inflation/deflation of the cuff is effected by a unit 42 under the control of the pneumatic control module 3. The pressure in the cuff is slowly reduced, and the breakthrough of blood through the cuff, which occurs once the arterial blood pressure is larger than the cuff pressure, is identified by the auscultatory method by means of Korotkoff sound identification by a microphone 43. It will be appreciated, however, that the blood pressure could be measured in other manners, e.g., the oscillometric method, by the identification of small pressure pulsations in the cuff, by a Doppler sensor, tonometer, etc. The standard measurement of the systolic and diastolic pressure is enhanced by using the Rodbard method. The resulted arterial blood pressure was demonstrated to be an approximation of the left-ventricular blood pressure.

The vascular flow measurement module 5 measures the flow in a large artery, such as the aorta, non-invasively by standard equipment, such as a commercial Echo-Doppler system (e.g., Sonos 1000 Hewlett-Packard, USA), or a chest impedance equipment (e.g., CDDP system, BoMED, California, USA). The measured signal may be directly acquired from the Doppler measurement apparatus (e.g., as an analog output of the velocity wave as supplied by a standard vascular Doppler device [e.g., the HD-207, Hadeco, Japan]), or it may be subject to further processing before it is acquired by the data-acquisition board via the Doppler conditioning module 6.

The velocity of the flowing blood is represented as a frequency shift of the ultrasonic wave as sensed by the Doppler sensor in module 5. This Doppler shift is measured by module 6 according to various known methods, such as analog signal analysis (e.g., by frequency-to-voltage conversion, zero-crossing counting), or digital signal analysis (e.g., fast Fourier transform algorithm), as commonly applied in commercial cardiologic Echo-Doppler apparatus.

The measured flow waves are used to calculate ventricular volumes as a function of time. However, instead of measuring flow rates the apparatus can be interfaced with commercial equipment for direct measurement of ventricular volumes such as a nuclear medicine gamma camera system (e.g., Apex system, Elscint, Israel), or new versions of echo-cardiographs which enable the on-line, automatic calculation and display of ventricular volume (e.g., Sonos 1500 with Acoustic Quantification, Hewlett-Packard, USA).

The electrocardiogram (ECG) measurement module 7 may be a standard ECG medical instrumentation which measures, preferably non-invasively, the electrical activity of the subject's heart. It normally contains a set of four electrodes which are applied to the subject's chest, and electronic circuitry which amplify and filter the signal.

The central processing unit CPU 8 may be a standard microcomputer, e.g., an IBM-compatible AT486 personal computer. It is used to control the operation of the above-described modules, to acquire data from the system sensors, to display the measured signals in real time in its display 8c, to analyze the measured data, and to make the various calculations, all as more particularly described below. In a typical configuration, it may include a microprocessor such as Intel 486, 8 MB of RAM memory, 130 MB hard disc, a floppy disc, a high resolution screen, and a screen adaptor.

The database 8b includes the subject identification data, the measured data and the results of the various calculations to be made as to be described below. These are saved in the system database 8b and are edited to produce the measurement report. The database 8b can be based on any standard software, e.g., Excel (Microsoft, USA), or on custom made software.

The data processor system including the CPU 8 also includes a real time module which acquires the measured signals via the data acquision board 9, processes them in real time (e.g., calibration to physical units), records them in the CPU memory, and displays them. In addition to data acquisition, the real time module controls the pneumatic system of the pneumatic module 2 which applies the external pressure pulsations on the subject's body.

The illustrated data processor system including the CPU 8 further includes an analysis module, which measures the various signals involved, including the R-wave trigger of the ECG signal from module 7, the pulsating pressure applied by the pneumatic module 2, the flow rate as sensed by the Doppler modules 5 and 6, and the blood pressure sensed by the blood pressure module 4. The pressure and flow rates are averaged and numerically processed to yield pressure-volume loops and various other indices of the cardiovascular system, during the operation of the system, as described more particularly below.

Figure 2:
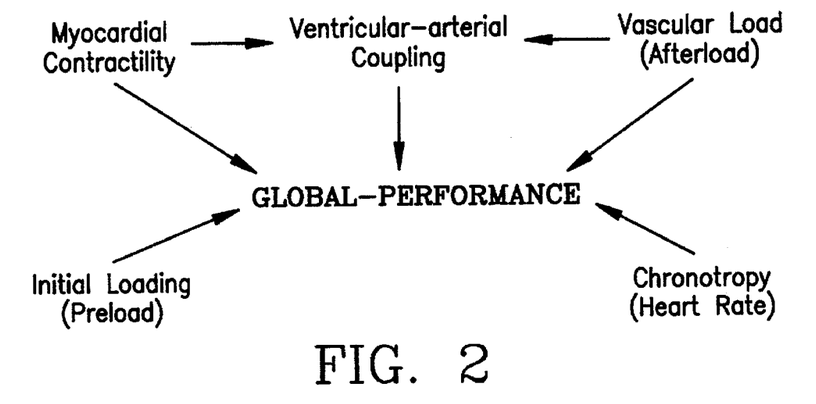
FIG. 2 is a diagram illustrating the determinants of the cardiovascular system performance.
Figure 3A:
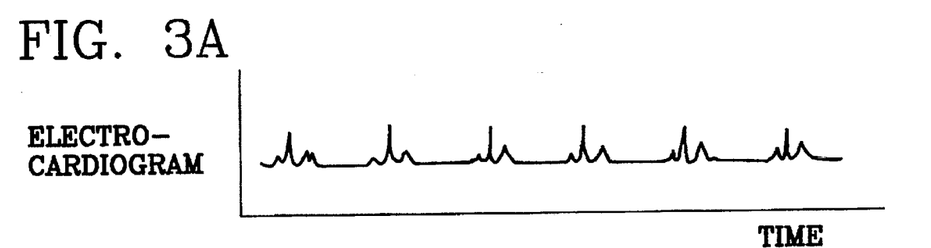
FIG. 3 illustrates a series of waveforms showing the effects of external pressure pulsations as applied in accordance with one described embodiment of the invention.
Figure 3B:
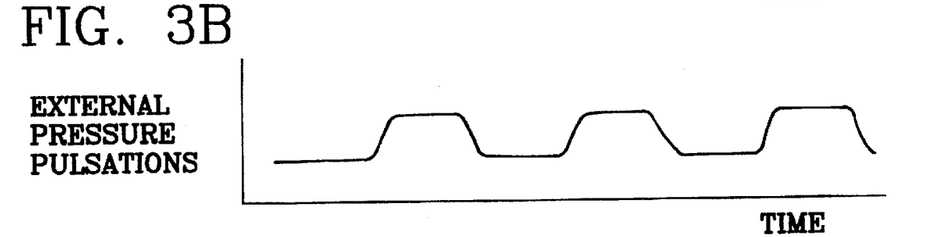
Figure 3C:
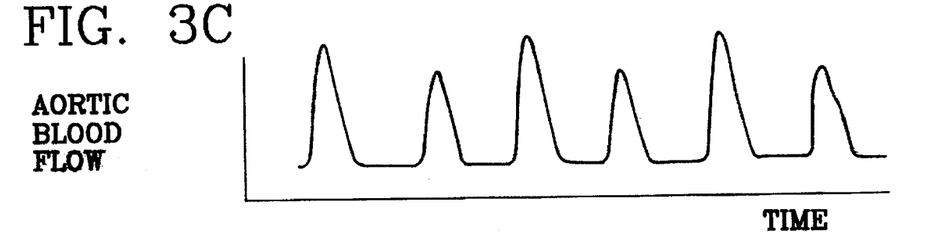
Figure 3D:
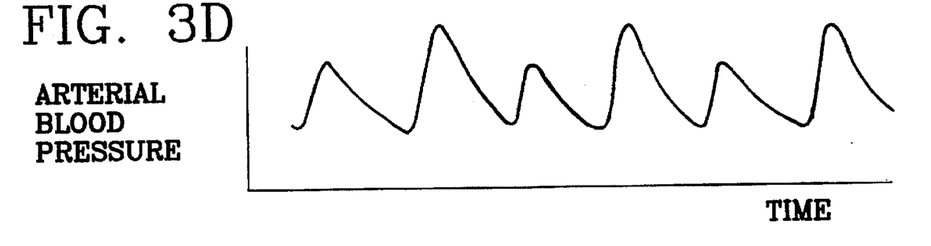

FIG. 2 illustrates the determinants of the cardiovascular system performance. Thus, as briefly described earlier and as more particularly illustrated in FIG. 2, the global performance of the cardiovascular system is based on four main determinants:

(a) myocardial contractility, namely the ability of the heart muscle elements to contract and create a force;

(b) initial loading, or ventricular preload, namely the initial length (or stress) of the muscular fibers, and is dependent on the state of filling of the heart;

(c) vascular load, or afterload, namely the load against which the heart acts; and (d) chronotropy, or heart rate, namely the number of cycles of heart contraction per unit time.

The present invention is mainly directed to assessing the first of the above determinants, myocardial contractility; this is relatively independent of the other determinants. More particularly, the present invention is primarily directed to determining, in accordance with a non-invasive technique, the ventricular elastance or end-systolic elastance (Ees) and the preload recruitable stroke work (PRSW), which have been previously suggested as indexes of myocardial contractility.

Following is a description of one manner of using the apparatus illustrated in FIG. 1 for assessing the cardiovascular performance of a subject in accordance with the present invention.

The pneumatic module 2, and particularly its pulsating pressure applicator 21, is used for applying external pressure pulsations on a peripheral organ of the subject (e.g., on the lower limbs and/or on the abdomen) of a sufficiently high level to alter ventricular loading. These external pressure pulsations are applied periodically once for every two or more heart cycles, as synchronized by the R-wave of the ECG signal. The ECG signal is illustrated by curve A in FIG. 3, and the external pressure pulsations are illustrated by curve B. It will be seen that the external pressure pulsations are applied for every other heart cardiac cycle, and for the complete respective cycle; however, such pulsations may be applied for several consecutive cycles, as illustrated in FIG. 8. The hemodynamic effect of the external pressure pulsations depends on the magnitude and the timing of the pulsations. In the above-described embodiment, relatively high magnitude pressure pulsations (of 150–180 mm Hg) are applied during one cycle and are released during the following cycle.

Each external high pressure pulsation results in an increased arterial pressure which impedes the ventricular ejection. The ventricular ejection during such a higher level of arterial pressure results in higher left-ventricular pressure and lower flow and stroke volume, as compared to the ventricular ejection during a lower level of arterial pressure. Thus, in the heart cardiac cycles during which the external pressure pulsations are applied, the arterial blood pressure is high and the aortic flow rate is low as compared to the heart cardiac cycles during which the external pressure pulsations are now not applied. The foregoing are illustrated by curves C and D in FIG. 3.

Figure 4A:
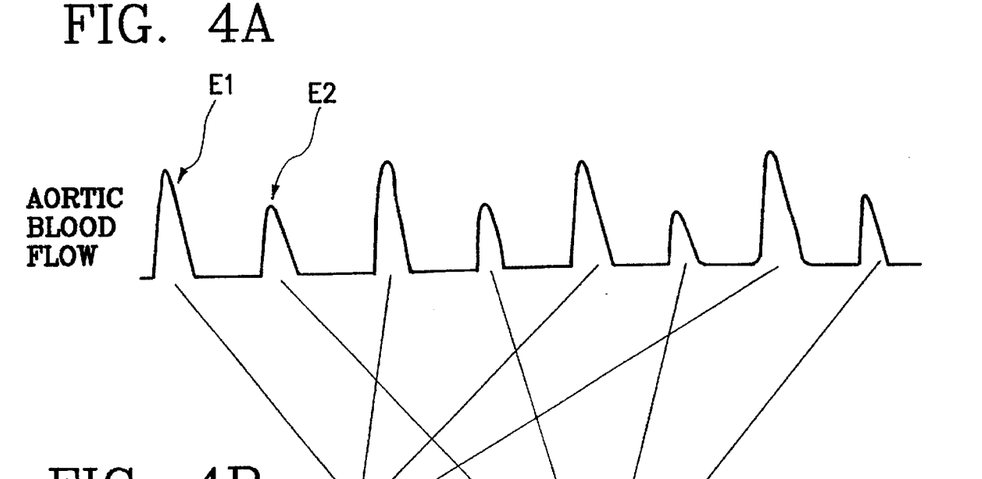
FIGS. 4A and 4B are waveforms illustrating the aortic flow during the performance of the assessment method in accordance with the present invention.

FIG. 4A illustrates the aortic flow both during the absence of the external pressure pulsations (amplitudes $E_1$) and during the presence of the external pressure pulsations (amplitudes $E_2$). The flow rate is measured by the Doppler modules 5 and 6 in FIG. 1.

Figure 4B:
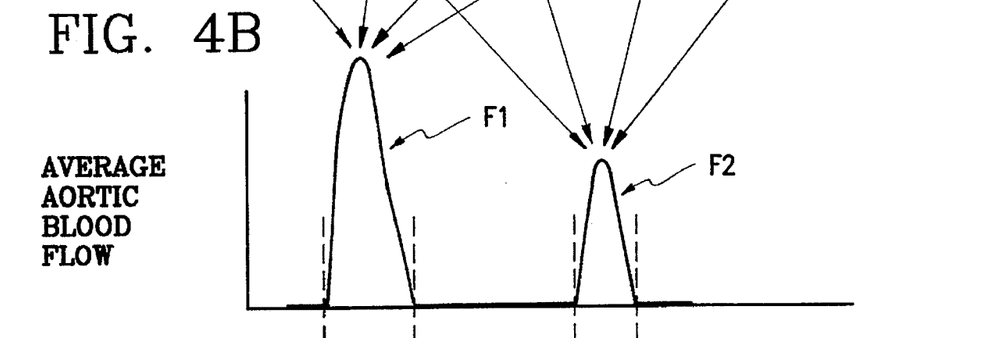

The measurement process continues for about 30–60 seconds. This normally spans 35–70 cycles during rest and up to 90–180 cycles during maximal stress (e.g., exercise stress test). The amplitudes $E_1$ and $E_2$ are averaged separately for the complete measurement period to yield two average flow waves $F_1$, $F_2$, respectively, as shown in FIG. 4B. The average flow waves are then integrated in the time domain to yield the ejected volume of the left ventricle as a function of time.

The end-disatolic volume may be measured by an external aparatus, e.g., a gamma-camera or an Echo-Doppler. The ventricular volume as a function of time during ejection can then be calculated by subtracting the ejected volume from the end-diastolic volume.

Figure 4C:
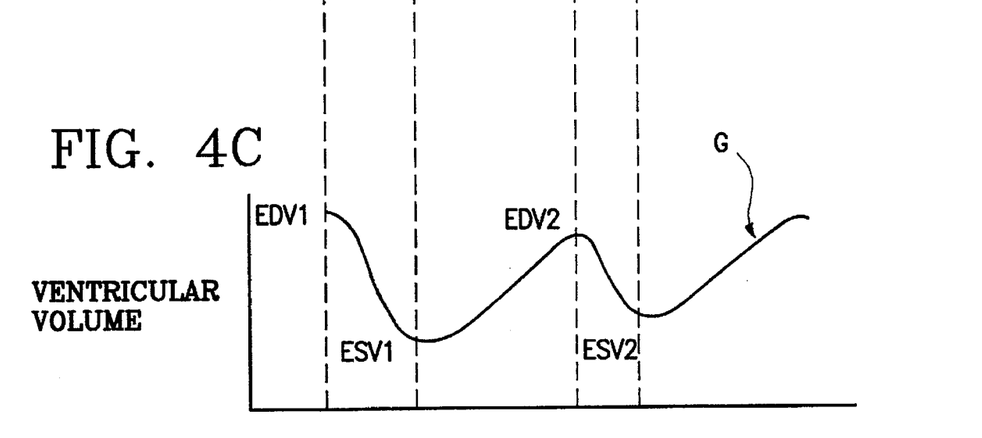
FIG. 4C illustrates the resultant ventricular volume.

The foregoing is more particularly illustrated in FIG. 4C, wherein curve G illustrates the ventricular volume as a function of time, points $EDV_1$ and $EDV_2$ represent the end diastolic volume, and points $ESV_1$ and $ESV_2$ represent the end-systolic volume.

Figure 5A:
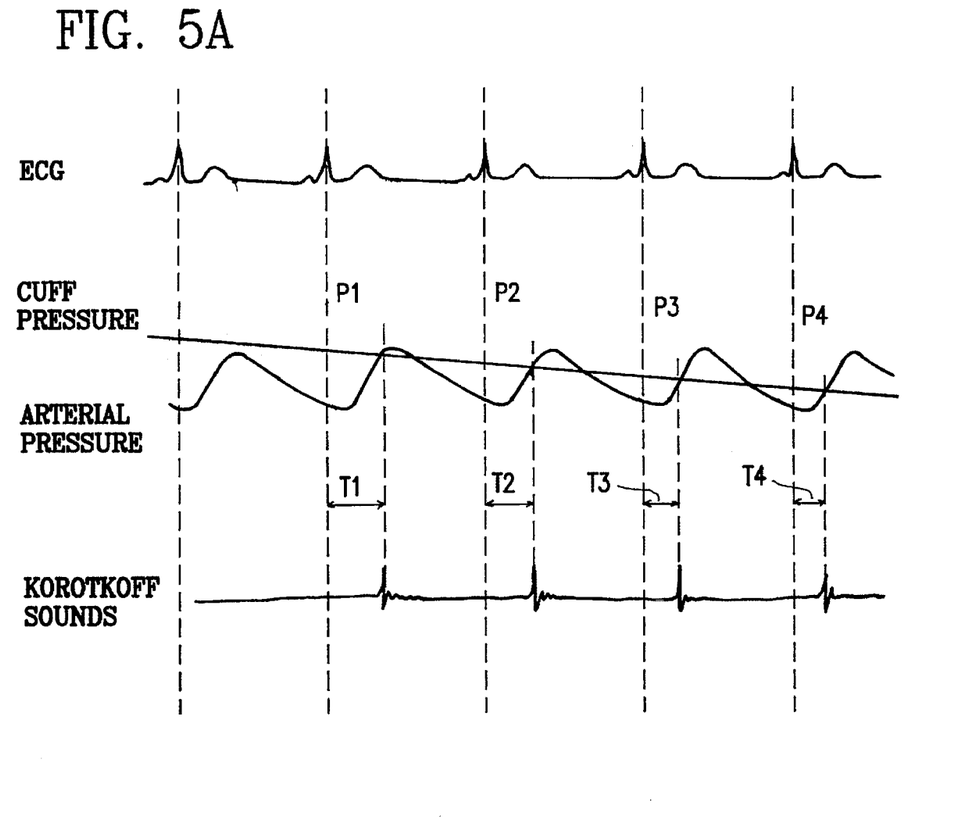
FIGS. 5A and 5B illustrate a technique for reconstructing a pressure wave.
Figure 5B:
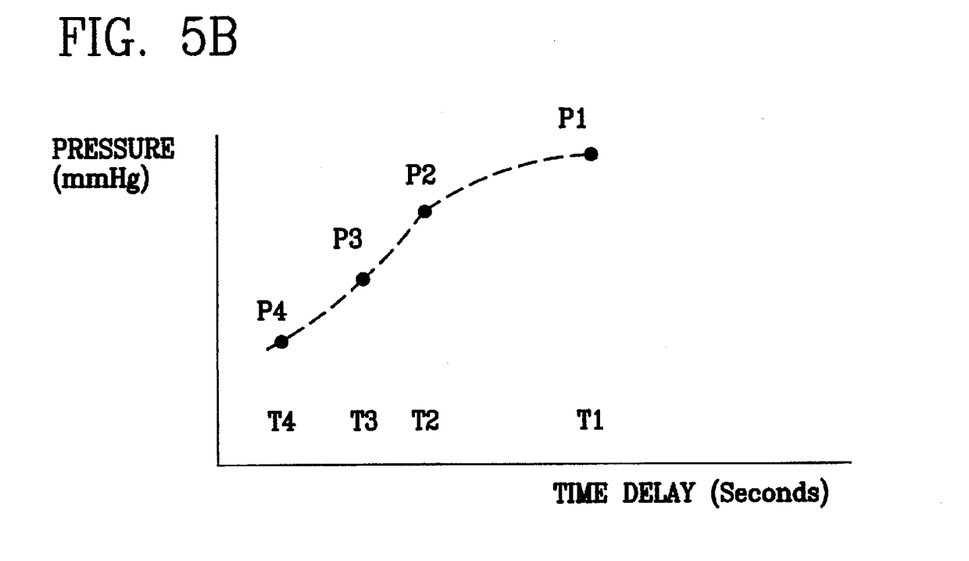

FIGS. 5A and 5B illustrate a known non-invasive method for reconstructing the rising part of an arterial pressure wave by using an occluding cuff, such as cuff 42 in the blood pressure module 4. Thus, the pressure in the occluding cuff is measured at the time of blood breakthrough across the occlusion. The breakthrough of blood, which occurs once the arterial pressure exceeds the pressure in the occluding cuff, may be determined by various methods and sensors; in the example illustrated in FIG. 5A, this is determined by the Korotkoff sounds, as sensed by microphone 43 in FIG. 4. The time delay between the time of heart contraction, as determined by the R-wave of the ECG, and the time of blood breakthrough is calculated, and the cuff pressure versus time delay is plotted. This results in a reconstructed upstroke portion of the arterial pressure wave, as shown in FIG. 5B.

Figure 6A:
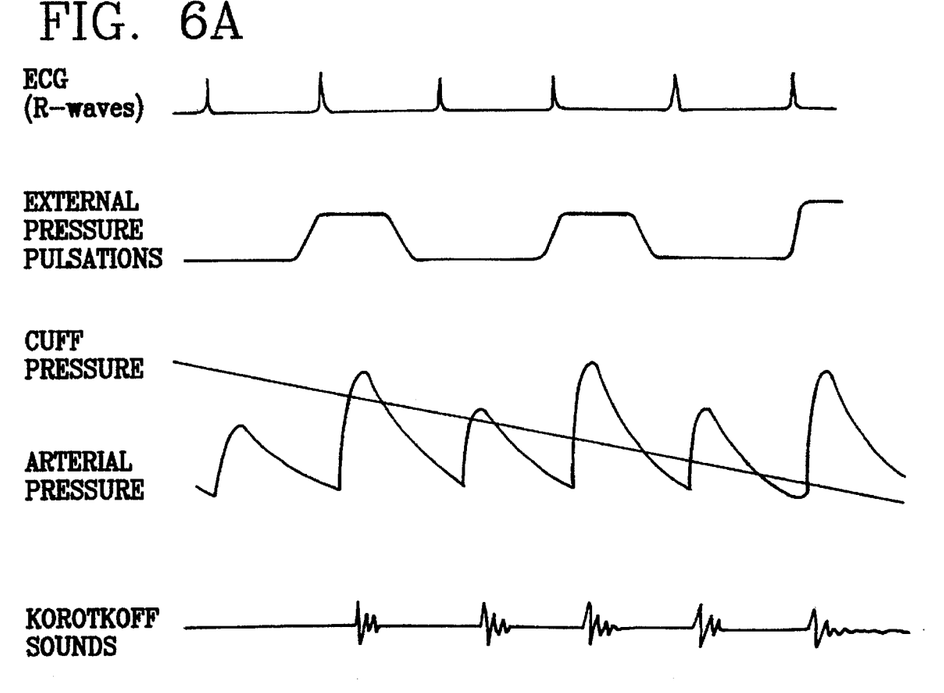
FIGS. 6A and 6B illustrate the technique of FIGS. 5A and 5B for reconstructing the pressure waves in accordance with the present invention.
Figure 6B:
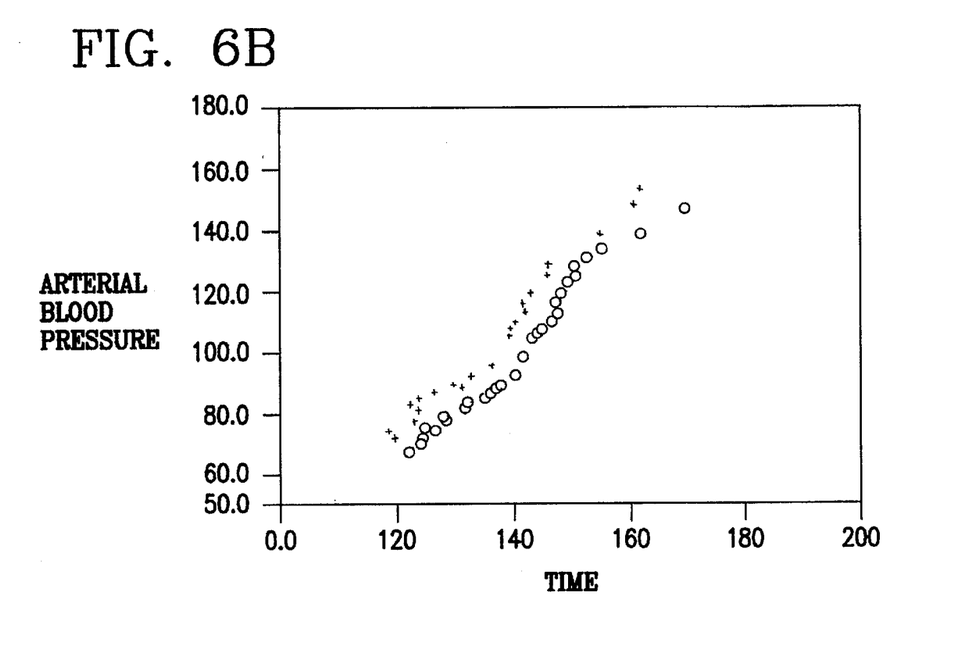

FIGS. 6A and 6B illustrate the foregoing technique for reconstructing the rising part of the arterial pressure waves during the heart cardiac cycles wherein the external pressure pulsations are applied, and also during the heart cardiac cycles wherein the external pressure pulsations are not applied. The two pressure waves so reconstructed, as shown in FIG. 6B, may then be extrapolated to the end-systolic pressure point according to known techniques. The time of end-systole (end ejection) may be determined from the average flow waves of FIG. 4B.

Figure 7A:
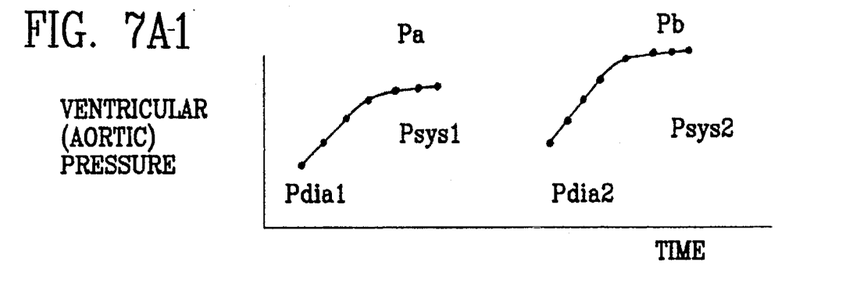
FIG. 7A illustrates the manner of reconstructing the pressure-volume loop in the method described herein.
FIG. 7B illustrates the manner of determining the ESPVR (end-systolic pressure volume relation) in the described method, to provide an accepted approximation of the ventricular elastance of the subject's heart.
Figure 7A:
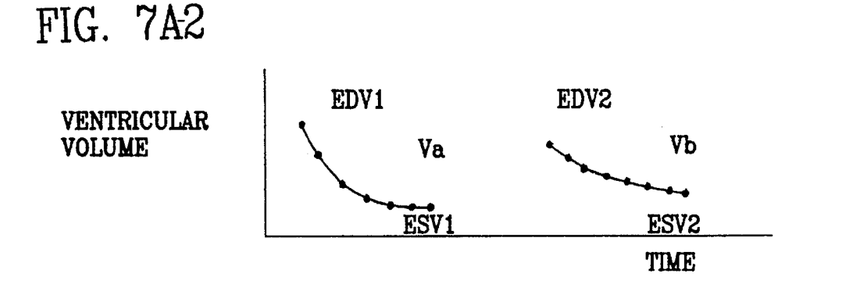

Two pressure-volume loops can be reconstructed from the pressure curves of FIG. 6B and the volume curves of FIG. 4C. Thus, the reconstructed pressure wave (FIG. 6B) and the calculated volume waves (FIG. 4C) are aligned together in time, as shown in FIG. 7A. Couples of pressure and volume data points are taken at sequential times and are used to construct the pressure-volume loop illustrated in FIG. 7B.

Figure 7B:
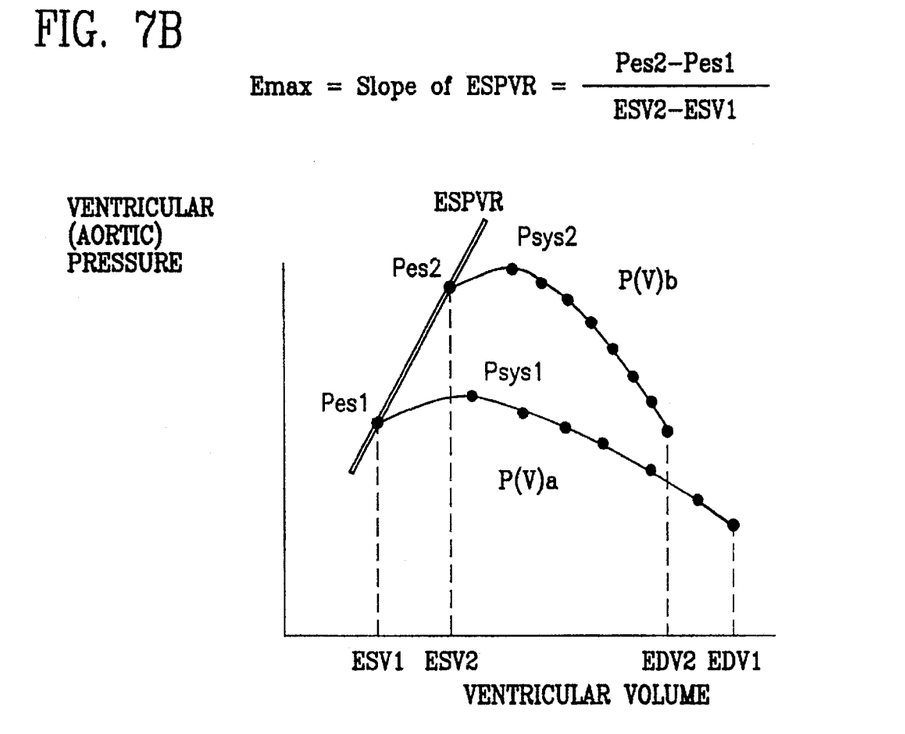
Figure 8A:
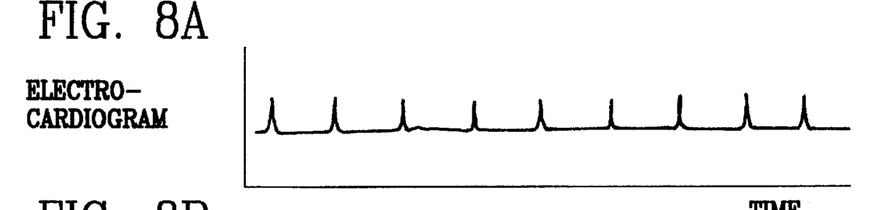
FIG. 8 illustrates a series of waveforms showing the effects of external pressure pulsations as applied in accordance with another described embodiment of the invention.
Figure 8B:
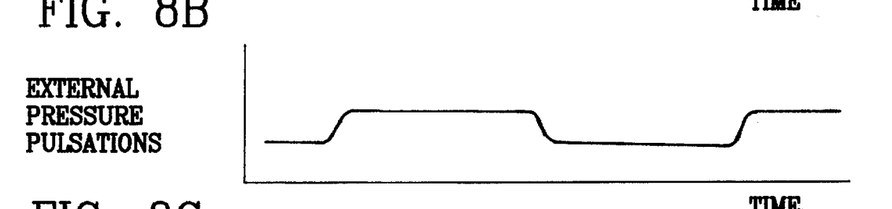
Figure 8C:
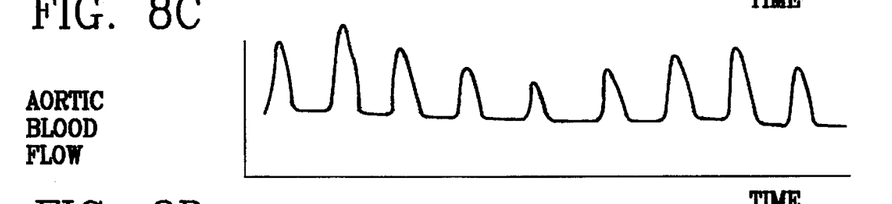
Figure 8D:
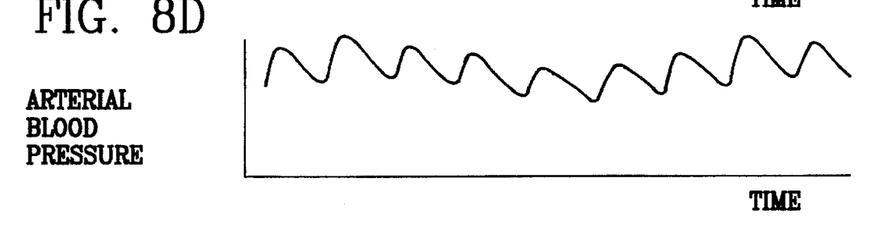

The pressure-volume loops of FIG. 7B can be used to derive the end-systolic pressure-volume relation, ESPVR, as also shown in FIG. 7B. The ESPVR is determined during (a) the cardiac cycles in which the external pressure pulsations are applied, and (b) the cardiac cycles during which the external pressure pulsations are not applied. For this purpose, the data processor: (1) produces a measurement (Va) of the volume of the heart left ventricle as a function of time during the cardiac cycles (a), and a corresponding measurement (Vb) during the cardiac cycles (b); (2) constructs from the measurements of the arterial pressure at least a portion (Pa) of the approximate left-ventricular blood pressure wave during the cardiac cycles (a) and a corresponding portion (Pb) of the pressure wave during the cardiac cycles (b); (3) determines from the measurements Pa, Va and Pb, Vb (FIG. 7A) the relations P(V)a and P(V)b (FIG. 7B) of ventricular blood pressure with respect to ventricular volume during the heart cardiac cycles (a) and (b), respectively; and (4) determines from the relations P(V)a and P(V)b, the ESPVR during the heart cardiac cycles (a) and (b), respectively. The data processor produces measurements (Va) and (Vb) by measuring the average aortic flow during the heart cardiac cycles (a) and (b), and by integrating the average aortic flows over the plurality of heart cardiac cycles or by getting direct measurement of ventricular volumes from an external apparatus. The slope of the ESPVR may then be determined. This slope provides a well accepted approximation of the ventricular elastance of the subject.

Figure 9:
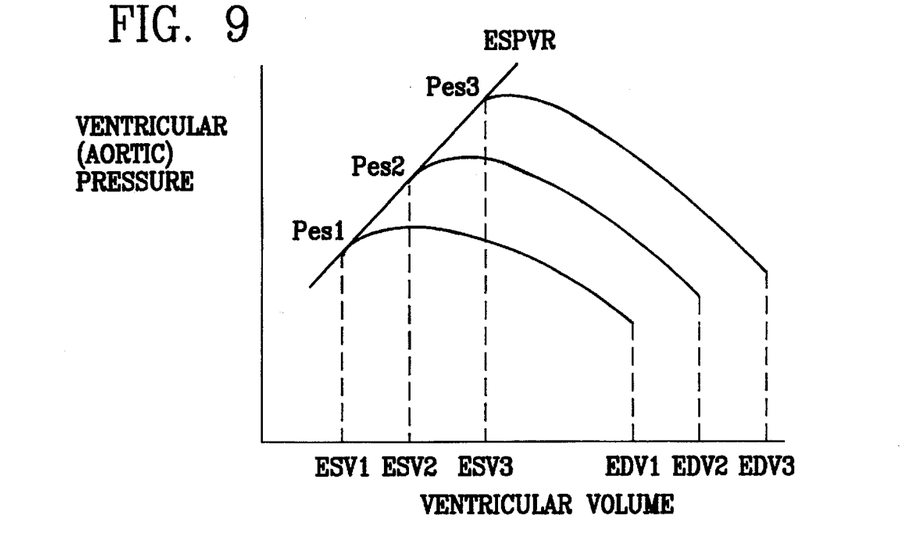
FIG. 9 illustrates the manner of reconstructing the pressure-volume loop in the embodiment illustrated in FIG. 8.

FIGS. 8 and 9 illustrate a second preferred embodiment wherein low magnitude pressure pulsations (50–80 mm Hg) are applied during a plurality ($N_1$) cardiac cycles over the abdomen and are released during a plurality ($N_2$) of the following cardiac cycles. The pressure pulsation increases the abdominal pressure and occludes transiently the inferior vena-cava. This maneuver reduces the venous return to the right ventricle, which reduces the ventricular volume and pressure. This direct effect on the right ventricle is transmitted to the left ventricle and yields periodically changing left ventricular volumes, ejection flows, and pressures as illustrated in FIG. 8. The flows, volumes and pressures are measured similarly as described earlier for pressure pulsation of one cardiac cycle duration. It should be noted, however, that more than two pressure-volume loops are acquired, as illustrated in FIG. 9.

It will thus be seen that the illustrated apparatus and method can be used for the non-invasive measurement of CVS indices in general, and the ventricular elastance in particular. The illustrated apparatus and method can also be used to assess the CVS status in patients with various heart diseases and clinical states, e.g., ischemic heart disease, congestive heart failure, dilated cardiomyopathy. The apparatus and method can also be used to monitor the effects of therapy, e.g., medications and rehabilitation activity.

I claim:

1. A method of assessing the cardiovascular performance of a subject, comprising:

applying periodically, for at least one complete heart cardiac cycle and in synchronism with every $n^{th}$ heart cardiac cycle wherein "n" is at least two, external pressure pulsations, by a pressure applicator applied externally of the subject's body, on a peripheral organ of the subject sufficient to alter ventricular loading;

acquiring data representative of the ventricular pressure, and data representative of the ventricular volume, of the subject's heart over a plurality of heart cardiac cycles;

and utilizing said data for assessing the cardiovascular performance of the subject.

2. The method according to claim 1, wherein said external pressure pulsations are applied during every other heart cardiac cycle, such that n=2.

3. The method according to claim 1, wherein said external pressure pulsations are applied during a plurality ($N_1$) cardiac cycles, and are released during a plurality ($N_2$) cardiac cycles, such that $n=N_1+N_2$.

4. The method according to claim 1, wherein said acquired data is utilized for assessing the cardiovascular performance of the subject by:

determining the end systolic pressure volume relation (ESPVR) of the subject's heart during (a) the heart cardiac cycles in which said external pressure pulsations are applied, and (b) the heart cardiac cycles in which the external pressure pulsations are not applied;

and determining the slope of the ESPVR during the heart cardiac cycles (a) and (b) to thereby provide an approximation of the ventricular elastance of the subject's heart.

5. The method according to claim 4, wherein, in order to determine the ESPVR, the acquired data includes a measurement (Va) of the volume of the heart left ventricle as a function of time during said heart cardiac cycles (a), and a corresponding measurement (Vb) during the heart cardiac cycles (b);

the acquired data also includes measurements of the arterial blood pressure, being used to construct at least a portion (Pa) of the arterial pressure wave during the cardiac cycles (a), and a corresponding portion (Pb) of the left ventricular pressure wave during the cardiac cycles (b);

determining from said portions (Pa) and (Pb) the relations P(V)a and P(V)b of ventricular pressure with respect to ventricular volume during the heart cardiac cycles (a) and (b), respectively;

and determining from said relations P(V)a and P(V)b the ESPVR during the cardiac cycles (a) and (b), respectively.

6. The method according to claim 5, wherein measurements (Va) and (Vb) are made by measuring the average aortic flow during said cardiac cycles (a) and (b);

and integrating said average aortic flows over said plurality of cardiac cycles.

7. The method according to claim 1, wherein said external pressure pulsations are pneumatically applied.

8. The method according to claim 1, wherein said external pressure pulsations are applied to a limb and/or abdomen of the subject.

9. Apparatus for assessing the cardiovascular performance of a subject, comprising:

a pressure applicator and a control therefor for applying periodically, for at least one complete heart cardiac cycle and in synchronism with every $n^{th}$ heart cardiac cycle wherein "n" is at least two, external pressure pulsations on a peripheral organ of the subject sufficient to alter ventricular loading;

sensors for sensing parameters of the subject varying with the left-ventricular blood pressure and the left-ventricular volume of the subject's heart, and for producing outputs corresponding to said sensed parameters;

and a data processor for processing the outputs of said sensors and for producing data representative of the left-ventricular blood pressure and the left-ventricular volume of the subject's heart over a plurality of heart cardiac cycles and useful in assessing the cardiovascular performance of the subject.

10. The apparatus according to claim 9, wherein said data processor processes the outputs of said sensors: to determine the end systolic pressure volume relation (ESPVR) of the subject's heart during (a) the heart cardiac cycles in which said external pressure pulsations are applied, and (b) the cardiac cycles during which the external pressure pulsations are not applied; and also to determine the slope of the ESPVR during the heart cardiac cycles (a) and (b), to thereby provide an approximation of the ventricular elastance of the subject's heart.

11. The apparatus according to claim 10, wherein said data processor: produces a measurement (Va) of the volume of the heart left ventricle as a function of time during said cardiac cycles (a), and a corresponding measurement (Vb) during the cardiac cycles (b); constructs from said left-ventricular blood pressure data at least a portion (Pa) of the pressure wave during the cardiac cycles (a) and a corresponding portion (Pb) of the pressure wave during the cardiac cycles (b); determines from said measurements Pa, Va and Pb, Vb the relations P(V)a and P(V)b of left-ventricular blood pressure with respect to ventricular volume during the heart cardiac cycles (a) and (b), respectively; and determines from said relations P(V)a and P(V)b, the ESPVR during the heart cardiac cycles (a) and (b), respectively.

12. The apparatus according to claim 11, wherein said data processor produces measurements (Va) and (Vb) by measuring the average aortic flow during said heart cardiac cycles (a) and (b), and by integrating the average aortic flows over the plurality of heart cardiac cycles.

13. The apparatus according to claim 9, wherein said pressure applicator is a pneumatic device.

14. Apparatus for assessing the cardiovascular performance of a subject, comprising:

a pressure applicator and a control therefor for applying periodically, for at least one complete heart cardiac cycle and in synchronism with every $n^{th}$ heart cardiac cycle wherein "n" is at least two, external pressure pulsations on a peripheral organ of the subject sufficient to alter ventricular loading;

a pressure sensor for sensing the aortic pressure of the subject;

a flow rate sensor for sensing the aortic flow rate of the subject;

and a data processor for processing outputs from the pressure sensor and flow rate sensor, and for producing data representative of the ventricular pressure, and data representative of the ventricular volume, of the subject's heart over a plurality of heart cardiac cycles, which data useful in assessing the cardiovascular performance of the subject.

15. The apparatus according to claim 14, wherein said data processor processes the outputs of said sensors:

to determine the end systolic pressure volume relation (ESPVR) of the subject's heart during (a) the cardiac cycles in which said external pressure pulsations are applied, and (b) the cardiac cycles during which the external pressure pulsations are not applied;

and also to determine the slope of the ESPVR during the heart cardiac cycles (a) and (b), to thereby provide an approximation of the ventricular elastance of the subject's heart.

16. The apparatus according to claim 15, wherein said data processor:

produces a measurement (Va) of the volume of the heart left ventricle as a function of time during said cardiac cycles (a), and a corresponding measurement (Vb) during the cardiac cycles (b);

constructs from said left-ventricular blood pressure data at least a portion (Pa) of the pressure wave during the cardiac cycles (a) and a corresponding portion (Pb) of the pressure wave during the cardiac cycles (b);

determines from said measurements Pa, Va and Pb, Vb the relations P(V)a and P(V)b of ventricular pressure with respect to ventricular volume during the heart cardiac cycles (a) and (b), respectively;

and determines from said relations P(V)a and P(V)b, the ESPVR during the heart cardiac cycles (a) and (b), respectively.

17. The apparatus according to claim 16, wherein said data processor produces measurements (Va) and (Vb) by measuring the average aortic flow during said heart cardiac cycles (a) and (b), and by integrating the average aortic flows over the plurality of heart cardiac cycles.

18. The apparatus according to claim 14, wherein said pressure applicator is a pneumatic device.

* * * * *